United States Patent
O'Heeron

(10) Patent No.: US 10,206,954 B2
(45) Date of Patent: Feb. 19, 2019

(54) ADIPOSE CELLS FOR CHONDROCYTE APPLICATIONS

(71) Applicant: SpinalCyte, LLC, Houston, TX (US)

(72) Inventor: Pete O'Heeron, Houston, TX (US)

(73) Assignee: SpinalCyte, LLC, Houston, TX (US)

(*) Notice: Subject to any disclaimer, the term of this patent is extended or adjusted under 35 U.S.C. 154(b) by 884 days.

(21) Appl. No.: 14/304,247

(22) Filed: Jun. 13, 2014

(65) Prior Publication Data

US 2014/0377231 A1 Dec. 25, 2014

Related U.S. Application Data

(60) Provisional application No. 61/836,975, filed on Jun. 19, 2013.

(51) Int. Cl.
- *C12N 5/00* (2006.01)
- *A61K 35/32* (2015.01)
- *C12N 5/077* (2010.01)

(52) U.S. Cl.
CPC ............ *A61K 35/32* (2013.01); *C12N 5/0655* (2013.01); *C12N 2506/13* (2013.01)

(58) Field of Classification Search
CPC ...................................................... C12N 5/00
See application file for complete search history.

(56) References Cited

U.S. PATENT DOCUMENTS

| | | | |
|---|---|---|---|
| 5,736,372 A | 4/1998 | Vacanti et al. | |
| 5,899,937 A | 5/1999 | Goldstein et al. | |
| 6,197,586 B1 | 3/2001 | Bhatnagar et al. | |
| 6,489,165 B2 | 12/2002 | Bhatnagar et al. | |
| 6,530,956 B1 | 3/2003 | Mansmann | |
| 6,627,422 B1 | 9/2003 | Li et al. | |
| 6,916,640 B2 | 7/2005 | Yu et al. | |
| 7,850,983 B2 | 12/2010 | Sevrain et al. | |
| 8,043,614 B2 | 10/2011 | Ahlfors | |
| 2002/0029083 A1 | 3/2002 | Zucherman et al. | |
| 2002/0094569 A1 | 7/2002 | Yu et al. | |
| 2002/0106625 A1 | 8/2002 | Hung et al. | |
| 2002/0115647 A1 | 8/2002 | Halvorsen et al. | |
| 2002/0159982 A1 | 10/2002 | Bonassar et al. | |
| 2003/0229400 A1 | 12/2003 | Masuda et al. | |
| 2004/0137613 A1 | 7/2004 | Vacanti et al. | |
| 2004/0166096 A1* | 8/2004 | Kolkin .................. | C12N 5/0653 424/93.7 |
| 2004/0191900 A1 | 9/2004 | Mizuno et al. ............. | 435/366 |
| 2004/0229886 A1 | 11/2004 | Bar et al. | |
| 2005/0002910 A1 | 1/2005 | Wolfinbarger et al. | |
| 2005/0019747 A1 | 1/2005 | Anderson et al. | |
| 2005/0074877 A1 | 4/2005 | Mao | |
| 2005/0090901 A1 | 4/2005 | Studer | |
| 2005/0153436 A1 | 7/2005 | Vilendrer | |
| 2006/0019362 A1 | 1/2006 | Yu et al. | |
| 2006/0147486 A1 | 7/2006 | Kim et al. | |
| 2007/0119126 A1 | 5/2007 | Anderson et al. | |
| 2007/0184033 A1 | 8/2007 | Sevrain et al. ............. | 424/93.7 |
| 2009/0068270 A1 | 3/2009 | Attawia et al. ............. | 424/484 |
| 2009/0148876 A1* | 6/2009 | Dodge .................. | C12N 5/0068 435/15 |
| 2009/0304644 A1 | 12/2009 | Hedrick et al. | |
| 2011/0112655 A1 | 5/2011 | Brekke et al. | |
| 2012/0010711 A1 | 1/2012 | Antonyshyn et al. | |

FOREIGN PATENT DOCUMENTS

| | | |
|---|---|---|
| JP | 2009528075 A | 8/2009 |
| WO | 9632076 | 10/1996 |
| WO | 9931221 A1 | 6/1999 |
| WO | 2001087323 A2 | 11/2001 |
| WO | 2004078954 | 9/2004 |
| WO | 2006011855 | 2/2006 |
| WO | 2007/092801 A2 | 8/2007 |
| WO | 2009048675 A1 | 4/2009 |
| WO | 2013070880 A1 | 5/2013 |
| WO | 2014204806 A2 | 12/2014 |

OTHER PUBLICATIONS

Shen et al. Int J Oral Sci 2011 3:117-124 "Dedifferentiated fat cells: an alternative source of adult multipotent cells from the adipose tissues".*
Matsumoto et al. Journal of Cellular Physiology 2008 215:210-222 "Mature Adipocyte-Derived Dedifferentiated Fat Cells Exhibit Multilineage Potential".*
Katsuya, Sadamori, et al.; Patent Abstract of Japan; "Viable Tissue Supplementation Material and Viable Tissue Supplementation Body"; Publ. No. 2005-237714; Sep. 8, 2005.
Elder, SH, et al.; "Cyclic Hydrostatic Compression Stimulates Chondroinduction of C3H/10T1/2 Cells"; Biomechan. Model Mechanobiol. (2005); 3:141-146.
Toh et al., "Application of a polyelectrolyte complex coacervation method to improve seeding efficiency of bone marrow stromal cells in a 3D culture system", Biomaterials. Jul. 2005;26(19):4149-60.
Bartkowiak et al., "Alginate-Oligochitosan Microcapsules: A Mechanistic Study Relating Membrane and Capsule Properties to Reaction Conditions", Chem. Mater., 1999, 2486-2492, vol. 11 (9).

(Continued)

*Primary Examiner* — Ruth A Davis
(74) *Attorney, Agent, or Firm* — Norton Rose Fulbright US LLP

(57) ABSTRACT

The present disclosure concerns methods and compositions for differentiating cells, including adipose cells, into chondrocyte-like cells via in vitro, ex vivo, and/or in vivo mechanical strain. In particular aspects, adipose cells or re-differentiated adipose cells that are chondrocyte-like cells, are delivered to a joint or are shaped into cartilage. In some embodiments, the adipose cells may be delivered to a joint, such as an intervertebral disc, following which the cells differentiate into chondrocyte-like cells to treat dysfunction of cartilage therein, including to repair degenerated discs, for example. In certain aspects, the cells prior to delivery to the individual are managed in the absence of growth factors, in vitro mechanical strain, and/or matrix molecules, for example.

50 Claims, No Drawings

(56) References Cited

OTHER PUBLICATIONS

Botchwey et al., "Tissue engineered bone: Measurement of nutrient transport in three-dimensional matrices", Journal of Biomedical Materials Research Part A, Published Online: 2003, 357-367, vol. 67A(1).
Chia et al., "Hepatocyte Encapsulation for Enhanced Cellular Functions", Tissue Engineering, 2000, 481-495; 6(5).
Endres et al., "Osteogenic Induction of Human Bone Marrow-Derived Mesenchymal Progenitor Cells in Novel Synthetic Polymer-Hydrogel Matrices", Tissue Engineering, 2003, 689-702; vol. 9(4).
Exploit Technologies Private Limited, "Macroencapsulation of Cells in 3D Scaffolds by Polyelectrolyte Complex Coacervation".
Kim et al., "Optimizing seeding and culture methods to engineer smooth muscle tissue on biodegradable polymer matrices", Biotechnology and Bioengineering, 46-54, Published Online: 2000, 46-54; vol. 57(1).
Li et al., "Effects of Filtration Seeding on Cell Density, Spatial Distribution, and Proliferation in Nonwoven Fibrous Matrices", Biotechnol. Prog., 2001, 935-944, vol. 17(5).
Moran et al., "Characterization of polylactic acid-polyglycolic acid composites for cartilage tissue engineering", Tissue Eng., 2003, 63-70, vol. 9(1).
Renken et al., "Microencapsulation: A review of polymers and technologies with a focus on bioartificial organs", Polimery, 1998, 530-539, vol. 43(9).
Ringe et al., "Stem cells for regenerative medicine: advances in the engineering of tissues and organs", Naturwissenschaften, 2002, Epub 2002, 23338-51, vol. 89(8).
Roberts et al., "Dopamine secretion by PC12 cells microencapsulated in a hydroxyethyl methacrylate-methyl methacrylate copolymer", Biomaterials, 1996, 267-275, vol. 17(3).
Schantz et al., "Repair of Calvarial Defects with Customized Tissue-Engineered Bone Grafts I. Evaluation of Osteogenesis in a Three-Dimensional Culture System", Tissue Engineering, 2003, 113-126, 9(supplement 1).
Wen, Shao et al., "Microcapsules through polymer complexation I: Complex coacervation of polymers containing a high charge density", Biomaterials, 1991, 374-384; vol. 12.
Sittinger et al., "Artificial tissues in perfusion culture", Int. J. Artif. Organs, 1997, 57-62, vol. 20(1).
Sittinger et al., "Encapsulation of artificial tissues in polyelectrolyte complexes: preliminary studies", Biomaterials, 1996, 1049-1051(3), vol. 17(10).
Toh et al., "A Configurable Three-Dimensional Microenvironment in a Microfluidic Channel for Primary Hepatocyte Culture", ASSAY and Drug Development Technologies. 2005, 169-176, vol. 3(2).
Uludag et al., "Technology of mammalian cell encapsulation", Advanced Drug Delivery Reviews, 2000, 29-64(36), vol. 42(1).
Ushida et al., "Three-Dimensional Seeding of Chondrocytes Encapsulated in Collagen Gel Into PLLA Scaffolds", Cell Transplantation, 2002, 489-494(6), vol. 11(5).
Wallace et al., "Collagen gel systems for sustained delivery and tissue engineering", Advanced Drug Delivery Reviews, 2003, 1631-1649(19), vol. 55(12).
Wen et al., "Microcapsules through polymer complexation—Part 3: encapsulation and culture of human Burkitt lymphoma cells in vitro", Biomaterials, 1995, 325-335(11), vol. 16(4).
Wendt et al., "Oscillating perfusion of cell suspensions through three-dimensional scaffolds enhances cell seeding efficiency and uniformity", Biotechnology and Bioengineering <http://www3.interscience.wiley.com/journal/71002188/home>, Published Online: 2003, 205-214, vol. 84(2).
Yang et al., "Novel cell immobilization method utilizing centrifugal force to achieve high-density hepatocyte culture in porous scaffold", Journal of Biomedical Materials Research, 379-386, Published Online: 2001, vol. 55(3).
Singh et al., "Chondrogenic differentiation of neonatal human dermal fibroblasts encapsulated in alginate beads with hydrostatic compression under hypoxic conditions in the presence of bone morphogenetic protein-2", Journal of Biomedical Materials Research Part A, Sep. 1, 2011, vol. 98A, Issue 3, pp. 412-424.
Mauck, R. L., "The role of cell seeding density and nutrient supply for articular cartilage tissue engineering with deformational loading", Osteoarthritis and Cartilage (2003), vol. 11 No. 12, pp. 879-890.
Kawanishi et al. "Effect of Three-Dimensional Culturing under Hydrostatic Pressure on Dedifferentiated Bovine Articular Chondrocytes", Jan. 6, 2000 J. Jpn. Orthop. Assoc., 2005, vol. 79, No. 8, p. S782.
Angele et al., "Cyclic hydrostatic pressure enhances the chondrogenic phenotype of human mesenchymal progenitor cells differentiated in vitro", J Orthop Res 21, 451, 2003.
French et al., "Chondrogenic Differentiation of Adult Dermal Fibroblasts", Annuals of Biomedical Engineering, Jan. 2004, vol. 32, No. 1, pp. 50-56.
Changwei, Lv "Repairing joint cartilage defects with three-dimension-induced autologous mesenchymal stem cells and related researchs" Chinese Doctoral Dissertations & Master's Theses Full-text Database (Doctor), Medicine and Health, 2004(04).
Oki, Yoshinao, et al; "Mature Adipocyte-Derived Dedifferentiated Fat Cells Can Trans-Differentiate into Osteoblasts in Vitro and in Vivo only by All-Trans Retinoic Acid"; Cell Structure andFunction 33: 211-222 (2008).
Sugihara, Hajime, et al; "Primary Cultures of Unilocular Fat Cells: Characteristics of Growth in Vitro and Changes in Differentiation Properties"; Differentiation, 31: 42-49 (1986).
Sloten, Audekercke, and van der Perre, "Biomechanica voor tissue engineering: kwantificeren van de mechanische belasting in de knie in vitro en in vivo" Katholieke Universiteit Leuven, 2000. (Partial English translation included).
Matsumoto et al. "Mature adipocyte-derived dedifferentiated fat cells exhibit multilineage potential", Journal of Cellular Physiology, vol. 215, No. 1, Apr. 1, 2008, pp. 210-222.
Shen et al. "Dedifferentiated fat cells: an alternative source of adult multipotent cells from the adipose tissues", International Journal of Oral Science, vol. 3, No. 3, Jul. 1, 2011, pp. 117-124.
Sakuma et al. "Mature, Adipocyte Derived, Dedifferentiated Fat Cells Can Differentiate Into Smooth Muscle-Like Cells and Contribute to Bladder Tissue Regeneration", Journal of Urology, vol. 182, No. 1, Jul. 1, 2009, pp. 355-365.
Kadiyala et al., "Culture Expanded Canine Mesenchymal Stem Cells Possess Osteochondrogenic Potential in Vivo and in Vitro", Cell Transplantation, vol. 6, No. 2, 125-134, 1997.
Sudo et al., "Mesenchymal Progenitors Able to Differentiate into Osteogenic, Chondrogenic, and/or Adipogenic Cells In Vitro Are Present in Most Primary Fibroblast-Like Cell Populations", Stem Cells 2007; 25: 1610-1617.
Kim et al., "Repair of cartilage defect in the rabbit with cultured mesenchymal stem cells from bone marrow", vol. 83-B, No. 2, Mar. 2001, pp. 289-294.

* cited by examiner

ADIPOSE CELLS FOR CHONDROCYTE APPLICATIONS

This application claims priority to U.S. Provisional Patent Application Ser. No. 61/836,975, filed Jun. 19, 2013, which is incorporated by reference herein in its entirety.

TECHNICAL FIELD

The field of the present disclosure includes at least the fields of medicine, surgery, anatomy, biology, cell biology and/or molecular biology. In certain embodiments the field of the disclosure concerns methods and compositions for treatment of medical conditions associated with body part(s) or tissues in need of cartilage or chondrocytes, for example.

BACKGROUND

Cartilage is a flexible connective tissue located in mammals in a variety of locations, including at least in joints between bones, the rib cage, the ear, the nose, the bronchial tubes and the intervertebral discs; it is a stiff material with less flexibility than muscle. Cartilage grows and repairs at a slower rate than other connective tissues, because cartilage does not contain blood vessels; instead, the chondrocytes are supplied by diffusion, helped by the pumping action generated by compression of the articular cartilage or flexion of the elastic cartilage. Furthermore, chondrocytes are bound in lacunae and cannot migrate to damaged areas, so cartilage damage is difficult to heal. The present disclosure at least provides solutions for needs in the art of cartilage repair.

SUMMARY

The present disclosure is directed to systems, methods, and compositions for treatment of an individual in need thereof, including treatment of an individual in need of cartilage repair, including repair of elastic cartilage, hyaline cartilage, or fibrocartilage, for example. The present disclosure concerns methods and compositions for biological repair of any kind of cartilage, including intervertebral and joint cartilage, for example. In particular aspects, the present disclosure concerns the fields of cartilage repair, such as articular cartilage repair. More particularly, embodiments of the disclosure includes methods for growing, proliferating, and/or differentiating cells into chondrocyte-like cells under mechanical stress, including doing so in vivo, ex vivo, or in vitro.

The present disclosure is directed to methods and compositions for cartilage engineering to generate cartilage for an individual in need thereof. In specific embodiments, the disclosure concerns cells and tissues for the treatment of cartilage deficiencies. It is an exemplary object of the present disclosure to provide methods to repair and/or regenerate cartilage. The methods of the present disclosure generate cartilage of any kind, including elastic cartilage, hyaline cartilage and/or fibrocartilage, which differ in the relative amounts of its main components.

Particular embodiments concern methods and compositions related to the use of adipose cells under mechanical strain to differentiate to chondrocyte-like cells. In certain aspects, the disclosure generates natural tissue in vivo, ex vivo, or in vitro, such as from adipose cells, for example. More particularly, but not exclusively, the present disclosure relates to a method for growing and differentiating mammalian (such as human) adipose cells into chondrocyte-like cells, for example. The cells may be autologous or allogeneic or a mixture thereof, in certain embodiments.

In specific embodiments, the disclosure employs differentiation of certain cells into chondrocyte-like cells. In specific embodiments, adipose cells, for example, are differentiated into chondrocyte-like cells under particular conditions. Differentiation of adipose cells into chondrocytes or chondrocyte-like cells may occur in any suitable manner, including differentiation in vivo following implantation of the cells or differentiation in vitro or ex vivo prior to implantation. The differentiated cells may be delivered to an individual as cells or as tissue generated from the cells, or a mixture thereof.

In specific embodiments the disclosure provides a method for in vivo regeneration of a joint, such as an intervertebral disc, elbow, knee, shoulder, hip, temporo-mandibular joint, and so forth. Cartilage tissue for a nose or ear may be generated, in some embodiments.

In certain embodiments, the cartilage that is the focus of application of the disclosure is intervertebral disc cartilage. In particular aspects of the disclosure, cells utilized in the disclosure are subjected to in vivo mechanical strain and other conditions found in the intervertebral disc for chondrogenic differentiation.

In one object of the present disclosure, there is provided a method for repairing a degenerated intervertebral disc, e.g. restore intervertebral disc anatomy and improve its functioning. In particular aspects of the disclosure, there is provided a method to repair one or more damaged discs. In one embodiment of the disclosure, there is a method of repairing damaged cartilage in a joint (such as an intervertebral disc) of an individual, comprising delivering adipose cells in accordance with the disclosure to the respective joint (such as intervertebral disc) of the individual. In specific embodiments of the disclosure, adipose cells (or adipose cells differentiated to chondrocyte-like cells in vitro and/or ex vivo) are delivered to the intervertebral disc in the absence of removing part or all of the degenerated disk. Under mechanical stress, the provided cells will acquire the characteristics of nucleus cells in the central part and annulus cells in the periphery, for example.

Embodiments of the disclosure include methods for growing, proliferating, and/or differentiating cells into chondrocyte-like cells under mechanical stress or other conditions found in the intervertebral disc space for the production of cartilage ex vivo that is then placed in vivo in an individual. In particular aspects of the disclosure, cells utilized in the disclosure are subjected to mechanical strain, low oxygen (for example, <5%), or both for chondrogenic differentiation. In some embodiments, there is a method of differentiating human adipose cells into chondrocyte-like cells ex vivo.

In certain aspects of the disclosure, the cells differentiate into chondrocyte cells or chondrocyte-like cells, such as wherein the chondrocyte cells or chondrocyte-like cells secrete a molecule selected from the group consisting of aggrecan, type II collagen, Sox-9 protein, cartilage link protein, perlecan, and combinations thereof. In particular cases, the cells are differentiated from adipose cells, and exemplary adipose cells include white adipose cells or brown adipose cells.

In specific embodiments, there are growth factors provided to the cells before, during, or after delivery of cells or tissue therefrom in vivo to the individual in need thereof, including growth factors such as bone morphogenetic protein 2 (BMP-2), BMP-4, BMP-6, BMP-7, cartilage-derived morphogenetic protein (CDMP), transforming growth factor beta (TGF-β), insulin growth factor one (IGF-I), fibroblast growth factors (FGFs), basic fibroblast growth factor (bFGF), FGF-2, platelet-derived growth factor (PDGF), and a mixture thereof; in alternative embodiments, these or other growth factors are not provided to the cells before, during, or after delivery of cells or tissue therefrom in vivo to the individual in need thereof.

In some embodiments of the disclosure, there are methods and compositions related to delivering adipose cells and/or re-differentiated adipose cells to a site in vivo in an individual in need thereof. In specific embodiments, the site is in vivo and in need of chondrocytes, including in need of cartilage. For example, a site in need of chondrocytes includes joints, for example cartilaginous joints (e.g., vertebrae). In some embodiments, the adipose cells and/or re-differentiated adipose cells are obtained from the individual in need of cartilage. In specific embodiments, adipose cells and/or re-differentiated adipose cells are delivered to at least one intervertebral disc in an individual. In some cases, the adipose cells and/or re-differentiated adipose cells are manipulated following being obtained, whether or not they are obtained from the individual in need thereof or whether or not they are obtained from a third party or commercially, for example. The adipose cells and/or re-differentiated adipose cells may be expanded in culture. In certain embodiments, the adipose cells and/or re-differentiated adipose cells are not provided growth factors, matrix molecules, mechanical strain, or a combination thereof, prior to or during or following implantation into a vertebrae.

In some embodiments, there are both adipose cells and/or re-differentiated adipose cells and chondrocytic cells in the disc. In some embodiments, not all adipose cells and/or re-differentiated adipose cells that are delivered in vivo will differentiate to chondrocytes in the disc, yet the tissues that are produced in the disc are nevertheless useful in improving the disc height and biomechanical function.

In some embodiments, there is a method of differentiating human adipose cells and/or re-differentiated adipose cells into chondrocyte-like cells in vivo, comprising the step of delivering adipose cells and/or re-differentiated adipose cells to a joint of an individual, wherein prior to delivering the adipose cells and/or re-differentiated adipose cells are not subjected to growth factors, matrix molecules, mechanical strain, or a combination thereof; in alternative embodiments, however, the adipose cells and/or re-differentiated adipose cells are subjected to growth factors, matrix molecules, mechanical strain, or a combination thereof. In specific cases, the individual has intevertebral disc disease. In some cases, the joint is an invertebral disc.

In some embodiments, some of the undifferentiated adipose cells and differentiated chondrocyte-like cells in the disc are further defined as cells that produce fibrous matrix molecules, cartilaginous matrix molecules, or both. In certain aspects, the chondrocyte-like cells are further defined as cells that produce matrix molecules, such as collagen I, collagen II, proteoglycan, or a combination thereof. In specific embodiments, the collagen comprises type I and type II collagen. In some cases, one of the proteoglycans is aggrecans.

In particular cases, the adipose cells and/or re-differentiated adipose cells are delivered between intervertebral discs. In certain cases, the adipose cells and/or re-differentiated adipose cells are delivered between or in nucleus pulposus and fissures in the inner annulus fibrosus.

Some aspects of methods of the disclosure include obtaining adipose cells from the individual or elsewhere. The obtaining may encompass removal of adipose cells from a body or may encompass retrieving already-obtained adipose cells, such as from a third party, including commercially, or from storage, for example. When the adipose cells are removed from a body, it may be from the thighs, hips, buttocks, abdomen, waist, upper arms, back, inner knee, chest area, cheeks, chin, neck, calves, and/or ankles.

In certain aspects, the adipose cells and/or re-differentiated adipose cells are expanded, for example for at least one day. In some cases, the obtained adipose cells are passaged, for example more than once. In particular aspects, the adipose cells are both expanded and passaged.

In some embodiments, there is a method of producing chondrocytic tissue in a joint of an individual, comprising the step of delivering adipose cells and/or re-differentiated adipose cells to the joint, wherein the adipose cells and/or re-differentiated adipose cells have not been exposed to growth factors, matrix molecules, mechanical strain, or a combination thereof, in vitro prior to or during or following delivery to the joint, although in alternative embodiments, the cells are exposed to growth factors, matrix molecules, mechanical strain, or a combination thereof, in vitro prior to or during or following delivery to the joint. In specific embodiments, the chondrocytic tissue comprise cells having particular biochemical markers, such as both type I and type II collagen and/or a number of proteoglycans found in cartilaginous and other tissues, for example.

In certain embodiments of the disclosure, the presence of the adipose cells and/or re-differentiated adipose cells and/or the death of adipose cells and/or re-differentiated adipose cells before and/or after delivery to the joint of the individual triggers response from one or more cells. In specific cases, the presence of the adipose cells and/or re-differentiated adipose cells and/or the death of adipose cells and/or re-differentiated adipose cells triggers response from other cells in the joint, and the other cells may be of any kind, including the individual's endogenous cells, such as chondrocytes, fibroblasts, adipose cells, disc stem cells, etc. In particular aspects, the endogenous cell response includes stimulation of growth, for example as at least some adipose cells and/or re-differentiated adipose cells die in the joint. Thus, in specific embodiments the mere presence of the adipose cells and/or re-differentiated adipose cells and/or release of intracellular factors upon death of cells may stimulate a cell growth response from existing cells in the disc. In particular cases, the cell growth response results in re-growth of the disc (or repair of the joint).

In particular embodiments of the disclosure, as an indirect or direct result of delivery of the adipose cells and/or re-differentiated adipose cells to the joint, scar tissue may form in the joint. In at least specific cases, such scar tissue formation is beneficial to the joint, for example when the joint is a disc, by providing stability, strength, cushion, seal of annular fissure(s) and so forth.

Thus, in certain aspects, the disclosure generates natural tissue ex vivo, such as from adipose cells, for example. More particularly, but not exclusively, the present disclosure relates to a method for growing and differentiating human adipose cells into chondrocyte-like cells (or cells that function in the same capacity as chondrocytes), for example. The cells may be autologous or allogeneic or a mixture thereof, in certain embodiments.

In specific embodiments, the disclosure employs differentiation of certain cells into chondrocyte-like cells or cells that function in the same capacity as chondrocytes. In specific embodiments, human adipose cells, for example, are differentiated into chondrocyte-like cells under particular conditions. Differentiation of cells into chondrocytes or chondrocyte-like cells may occur in any suitable manner, including ex vivo following procurement of adipose cells, such as commercially or from a living individual or cell or tissue bank. Exemplary adipose cells cells may be harvested from a biopsy or liposuction, for example. In some embodiments, the adipose cells are obtained from the individual in need of cartilage.

In some embodiments of the disclosure, cartilage tissue is generated from adipose cells. The cartilage may be imaged in an individual in need of cartilage repair or suspected of being in need of cartilage repair. Cartilage does not absorb x-rays under normal in vivo conditions, but a dye can be injected into the synovial joint that will cause the x-rays to be absorbed by the dye. The resulting void on the radiographic film between the bone and meniscus represents the cartilage. Other means of imaging cartilage is by magnetic resonance imaging (MRI). In embodiments of the disclosure, an image is taken of part of an individual to facilitate generation of cartilage tissue of a desired shape. In at least specific embodiments the image is three-dimensional. The imaging may be of any kind so long as it is suitable to allow generation of a desired cartilage shape. In specific embodiments, one could employ imaging, such as MRI or computed tomography (CT scan), of cartilage in a body location that is desired to be repaired or that is desired to be imaged to facilitate repair. For example, in cases where an ear or knee is in need of repair, one could take an image of a respective healthy ear or knee and produce an image (a mirror image, in the case of the ear) of desired cartilage tissue of same.

An individual in need of cartilage repair may be of any kind so long as there is a detectable deficiency in cartilage tissue of any kind in the individual. In specific embodiments the cartilage deficiency comprises cartilage loss. An individual needing cartilage repair may be in need because of injury, disease, birth defect, environmental chemical exposure, a desire for cosmetic plastic surgery, excessive and/or substandard plastic surgery, the effects of obesity, sudden trauma, repetitive trauma, degeneration caused by wear and tear, the result of hip dysplasia, abusive use of drugs, allergic reactions, or a combination thereof. In cases where there is injury, the injury may be of any kind, including from combat, a fight, sports, exercise, and/or immobility for extended periods of time, for example. If the need is the result of disease, the disease may be of any kind, including genetic, osteoarthritis, achondrogenesis, relapsing polychondritis, and so forth. The birth defect may be of any kind, such as microtia (including anotia), for example. An individual in need thereof may have a broken nose.

In certain aspects of the disclosure, the cells differentiate into chondrocyte cells or chondrocyte-like cells, such as wherein the chondrocyte cells or chondrocyte-like cells secrete a molecule selected from the group consisting of aggrecan, type II collagen, Sox-9 protein, cartilage link protein, perlecan, and combinations thereof. In particular cases, the cells are differentiated from adipose cells.

In specific embodiments, there are no growth factors provided to the adipose cells, including growth factors such as bone morphogenetic protein 2 (BMP-2), BMP-4, BMP-6, BMP-7, cartilage-derived morphogenetic protein (CDMP), transforming growth factor beta (TGF-β, insulin growth factor one (IGF-I), fibroblast growth factors (FGFs), basic fibroblast growth factor (bFGF), FGF-2, platelet-derived growth factor (PDGF), and a combination thereof. However, in alternative embodiments growth factors are employed in methods of the disclosure, such as provided to the adipose cells, chondrocytes, and/or cartilage tissue, including BMP-2, BMP-4, BMP-6, BMP-7, CDMP, TGF-β, IGF-I, FGFs, bFGF, FGF-2, PDGF, and a combination thereof. Other growth factors may be employed.

In some embodiments of the disclosure, there are methods and compositions related to delivering cartilage to a site in vivo in an individual in need thereof, wherein the cartilage was generated with a method of the disclosure. In specific embodiments, the delivery site is in vivo and in need of chondrocytes, including in need of cartilage. For example, a site in need of chondrocytes includes an ear, nose, knee, shoulder, elbow, and any other areas of the body where connective tissue is present or required. In some cases the cartilage is for a joint, whereas in other cases the cartilage is not for a joint.

In some embodiments, the adipose cells are obtained from the individual in need of cartilage. In specific embodiments, resultant chondrocytes generated from adipose cells are delivered to at least one location in an individual. In some cases, the adipose cells are manipulated following being obtained, whether or not they are obtained from the individual in need thereof or whether or not they are obtained from a third party or commercially, for example. The adipose cells may be expanded in culture. In certain embodiments, the adipose cells are not provided growth factors, matrix molecules, mechanical strain, or a combination thereof, prior to or during or following implantation into the individual, although in alternative embodiments the adipose cells are provided growth factors, matrix molecules, mechanical strain, or a combination thereof, prior to or during or following implantation into the individual.

Although the cartilage may be stored under suitable conditions for the individual from which the adipose cells were derived, in some cases the cartilage is stored under suitable conditions for an individual from which the adipose cells were not derived. The skilled artisan recognizes that in situations where the individual to which the cartilage is ultimately delivered is not the same individual that the original adipose cells were obtained, one or more steps may be taken to prevent tissue rejection by the host body.

In some embodiments, there are both adipose cells and chondrocytic cells in the cartilage. In some embodiments, the cartilage tissue is generated ex vivo but still retains one or more adipose cells. Such tissue may still be delivered in vivo.

Thus, in specific embodiments one could generate high definition/resolution MRI or CT scan or other diagnostic imaging modality images of cartilage in the knee, shoulder, elbow, nose, ear, etc. In some embodiments, the MRI image would be utilized to generate a three-dimensional mold of the desired cartilage shape. In some embodiments, the mold is seeded with human adipose cells according to the present disclosure. Thus, the mold is subjected to conditions that facilitate generation of chondrocytes from adipose cells, and in specific embodiments the conditions comprise low oxygen, mechanical stress, or any other atmospheric or biological condition(s) that may optimize differentiation of the adipose cells into chondrocytes or chondrocyte-like cells, or a combination thereof. In specific embodiments, the adipose cells to be differentiated to chondrocytes are exposed to a chamber that provides suitable conditions for chondrocyte differentiation. Within this environment, one can produce chondrocyte differentiation from adipose cells and produce the cartilage tissue in the mold. Once the tissue is generated, it can be placed in the body at the appropriate location. In specific embodiments, at least one support is employed to support the cartilage; in specific embodiments the support is resorbable, although in some cases the support is not resorbable and is effectively permanent for the individual. In some cases, titanium, polymer, or another material is employed to support the cartilage.

In certain aspects of the disclosure, an individual is provided another therapy in addition to the methods of the disclosure. For example, before, during, and/or after delivery of the adipose cells cells, the individual may receive one or more antibiotics. Exemplary post-operative therapies includes Non Steroidal Anti-Inflammatory Drugs (NSAIDs), simple pain killers (analgesics), and/or muscle relaxants as needed, and it may be followed by a functional rehabilitation post-operatively, such as after the first, second, third or more post-operative week, for example. In specific embodiments, the individual may be provided one or more of an antibiotic, antifungal agent, or antiviral agent.

In certain aspects of the disclosure, an individual is provided another therapy in addition to the methods of the disclosure. For example, before, during, and/or after delivery of the adipose cells or re-differentiated adipose cells, the individual may receive one or more drugs, such as antibiotics, painkillers, and so on. Exemplary post-operative therapies includes Non Steroidal Anti-Inflammatory Drugs (NSAIDs), simple pain killers (analgesics), and/or muscle relaxants as needed, and it may be followed by a functional rehabilitation post-operatively, such as after the first, second, third or more post-operative week, for example. In specific embodiments, the individual may be provided one or more of an antibiotic, antifungal agent, or antiviral agent.

In a further embodiment, there is a kit comprising adipose cells that are housed in one or more suitable containers. In specific embodiments, the kit further comprises one or more reagents suitable for enhancing in vitro, in vivo, ex vivo differentiation from adipose cells to chondrocytes or chondrocyte-like cells. In some embodiments, the kit of the disclosure includes one or more apparatuses for delivery of tissue or cells (including cartilage tissue) to an individual. In some cases, the kit comprises one or more supports for stabilization of the cartilage upon in vivo delivery of the ex vivo-generated cartilage.

In some embodiments of the disclosure, there is a method of inducing de-differentiation of adipose cells to chondrocyte-like cells, comprising the step of subjecting the adipose cells to mechanical strain. In specific embodiments, the subjecting step occurs in vitro or ex vivo or in vivo, or a combination thereof. In certain cases, the mechanical strain comprises low oxygen tension, intermittent hydrostatic pressure, fluid shear stress, any other mechanical or strain forces exerted in vivo on existing cartilage, or a combination thereof. The adipose cells may be white adipose cells, brown adipose cells, or a mixture thereof.

In aspects of the disclosure, when the adipose cells are subjected to mechanical strain in vitro, the cells are combined with a scaffold to produce a cells/scaffold composition. In some cases, the cells/scaffold composition comprises growth factors, matrix molecules, drugs, or a combination thereof. The cells/scaffold composition may be delivered to an individual, such as to the joint of an individual. In specific embodiments, the joint is an intervertebral disc. In certain cases, the individual has intervertebral disc disease.

In aspects of the disclosure, when the adipose cells are subjected to mechanical strain ex vivo, the cells are provided conditions suitable to generate cartilage. In specific embodiments, the conditions comprise low oxygen, mechanical stress, or a combination thereof. In some cases, the cartilage is configured in the form of a desired shape. The desired shape may be at least part of an ear or of a nose, for example. In some aspects, the method further comprises the step of generating a mold of the desired shape. In some cases, the method further comprises the step of providing the cartilage to an individual that is in need of cartilage repair. In specific embodiments, the desired shape is utilized to replace or repair cartilage in one or more regions of the body of an individual, wherein the region requires connective tissue. In certain embodiments, the method further comprises the step of imaging a part of the body of an individual that is in need of cartilage repair or that is suspected of being in need of cartilage repair. In some cases, the method further comprises the step of imaging a part of the body of an individual that is in need of cartilage repair and generating therefrom a mold of a desired shape of cartilage. In certain embodiments, the method further comprises the step of imaging a part of the body of an individual wherein that part is not in need of repair and using that image to generate a mold for growth of cartilage to replace or repair an area in need of repair.

When cartilage or tissue from adipose cells is provided to the individual, in some cases it may be done so with one or more supports. In specific embodiments, the support is resorbable. In some aspects, the support is comprised of a material that would be resorbed by the body of the individual during and/or after its function of cartilage formation is completed. In particular cases, the support is non-resorbable. In certain embodiments, the support is comprised of metal or one or more other materials that may remain in the body and act as a scaffolding to maintain shape and function of the cartilage.

When cartilage or tissue from adipose cells is delivered to a nose, ear, knee, shoulder, elbow or other area of the body, it may be done where connective tissue is required for the individual. In some cases, the cartilage or tissue from adipose cells is not delivered to a joint. In specific embodiments, the cartilage tissue is not delivered to a vertebral disc.

In aspects of the disclosure, when the adipose cells are subjected to mechanical strain in vivo, the adipose cells are not subjected to growth factors, matrix molecules, mechanical strain, or a combination thereof prior to the in vivo subjecting step. In particular embodiments, the adipose cells are delivered to a joint of the individual. In some cases, the individual has intevertebral disc disease. In specific embodiments, the cells are delivered to an intervertebral disc. In some embodiments, following delivery to the joint there is a mixture of adipose cells and chondrocyte-like cells in the joint. The chondrocyte-like cells may be further defined as cells that produce matrix molecules such as collagen I, collagen II, proteoglycan (such as aggrecans), or a combination thereof. The collagen may comprise type I and type II collagen.

When adipose cells are delivered to an individual, it may be between invertebral discs. In specific aspects, the adipose cells are delivered between or in nucleus pulposus and fissures in the inner annulus fibrosus.

Methods of the disclosure may further comprise obtaining adipose cells from the individual. In some cases, the obtained adipose cells are expanded, such as at least one day. In some cases, the obtained adipose cells are passaged, such as passaging more than once.

In certain embodiments, following delivery of the adipose cells to the joint of the individual, a plurality of adipose cells die. In specific embodiments, death of the adipose cells results in a cellular response from endogenous joint cells of the individual. In some embodiments, the cellular response comprises stimulation of growth of the endogenous joint cells of the individual. In certain aspects, following delivery of the adipose cells to the joint of the individual, there is development of scar tissue in the joint.

In embodiments of the disclosure, the adipose cells are autologous or allogeneic to the individual.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying FIGURES. It is to be expressly understood, however, that each of the FIGURES is provided for the purpose of illustration and description only and is not intended as a definition of the limits of the present invention.

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the disclosure may "consist essentially of" or "consist of" one or more elements or steps of the disclosure, for example. Some embodiments of the disclosure may consist of or consist essentially of one or more elements, method steps, and/or methods of the disclosure. It is contemplated that any method or composition described herein can be implemented with respect to any other method or composition described herein.

The term "adipose cells" (which may also be referred to as adipocyte or lipocytes or fat cell) as used herein refers to connective-tissue cells that are able to synthesize and contain large globules of fat. Two types of adipose cells include the following: 1) white adipose cells having large fat droplets, a small amount of cytoplasm, and flattened, non-centrally located nuclei; and 2) brown adipose cells having fat droplets of differing size, a large amount of cytoplasm, numerous mitochondria, and round, centrally located nuclei. The primary chemical constituents of adipose cell fat comprise triglycerides, which are esters made up of a glycerol and one or more fatty acids, such as stearic, oleic, or palmitic acids.

The term "chondrocyte-like cells" as used herein refers to cells that are not primary chondrocytes but are derived from adipose cells, for example. These chondrocyte-like cells have a phenotype of chondrocytes (cells of cartilage) including a shape of chondrocytes (polygonal and/or rhomboidal cells, for example) and/or are able to aggregate and produce cartilage matrix components, such as sulfated proteoglycan and type II collagen, for example. Thus, exemplary markers of chondrocyte-like cells include one or more of aggrecan, which is a chondroitin sulfate and keratan sulfate proteoglycan, type II collagen, Sox-9 protein, cartilage link protein, and perlecan, which is a heparan sulfate proteoglycan, for example.

The term "joint" as used herein refers to a region in the body wherein two bones of a skeleton join.

The term "re-differentiated adipose cells" as used herein refers to adipose cells that have been subjected to conditions to become chondrocyte-like cells. The conditions may be of any suitable kind, although in specific embodiments the mechanical conditions comprise hydrostatic pressure (including constant or intermittent), low oxygen, fluid shear stress, and so on.

The term "fluid shear stress" refers to the motion of fluids upon a surface, which results in the generation of shear stress. Shear stress is a stress state where the stress is parallel to a surface. Microfluidic scaffold allows fluid flow in the microchannels. This fluid flow induces fluid shear stress on the cells seeding in the scaffold.

The term "hermetic" as used herein refers to being made liquid-tight, such as by fusion or sealing, for example. In particular, a hermetic membrane does not allow liquid inside it to exit the membrane, although it allows oxygen and carbon dioxide to cross the membrane (such as oxygen to enter the membrane and carbon dioxide to leave the membrane).

The term "hydrostatic pressure" refers to the pressure exerted or transmitted by liquid (for example, water) at rest. The intervertebral disc is exposed to wide ranges of intradiscal hydrostatic pressure during different loading exercises and are at their minimum (about 0.25 MPa) during lying or relaxed sitting and at maximum (about 2.5 to 5 MPa) during lifting weights with a round back. These different loading magnitudes influence the intervertebral disc by alteration of disc matrix turnover depending on their magnitudes. Numerous studies have been done to determine the best regimen for intermittent hydrostatic pressure (IHP) to be applied in vitro to the cells to induce chondrogenic differentiation of cells in vitro. Different regimens have been tested. In these studies, IHP applied is within the amplitude ranges from 0.5 MPa to about 5 MPa and a frequency range from 0.01 Hz to 1 Hz. The encapsulating device is designed to transmit in vivo hydrostatic pressure to the cell-matrix construct, in specific embodiments. The external envelop filled with liquid (medium) is compressed during different loading exercises; under this compression some liquid medium diffuses through the semi-permeable internal membrane, which allows perfusion of the cell-matrix construct and generates hydrostatic pressure within the cell-matrix construct. In this system, the appropriate physiologic hydrostatic pressure is applied to the cell-matrix construct, which is useful for chondrogenic differentiation of the cells.

The term "hypoxia" as used herein refers to a deficiency in oxygen. In specific aspects, it refers to oxygen tension that is less than about 20%.

The term "joint" as used herein refers to a region in the body wherein two bones of a skeleton join.

I. General Embodiments

Although any tissues may be repaired at least in part by methods of the disclosure, including any cartilage tissues, in a particular exemplary embodiment, intervertebral disc cartilage or joint cartilage is repaired. A general embodiment of the disclosure is to use adipose cells as cell sourcing for engineering new cartilage for the intervertebral disc. The disclosure encompasses differentiation of these cells into chondrocyte-like cells.

In particular embodiments of the disclosure, the adipose cells may be differentiated to chondrocyte-like cells in one of a variety of ways, including ex vivo, in vitro, and/or in vivo. In specific embodiments, particular conditions are employed to facilitate differentiation of chondrocytes from adipose cells ex vivo, including, for example, the following: 1) three dimensionality; 2) low oxygen tension; and 3) mechanical stress; 4) intermittent hydrostatic pressure; 5) fluid shear stress; and/or 6) other outside conditions that are conducive to chondrogenic differentiation.

II. Cells Utilized in the Disclosure

In certain embodiments of the disclosure, any cell may be employed so long as the cell is capable of differentiating into a chondrocyte or chondrocyte-like cell. However, in specific embodiments, the cell is an adipose cell, for example. Autologous cells may be utilized, although in alternative embodiments allogeneic cells are employed; in specific embodiments, the allogeneic cells have been assayed for disease and are considered suitable for human transmission. In certain aspects of the disclosure, the cell or cells are autologous, although in alternative embodiments the cells are allogeneic. In cases wherein the cells are not autologous, prior to use in the disclosure the cells may be processed by standard means in the art to remove potentially hazardous materials, pathogens, etc.

Adipose cells may be harvested using a surgical resection or liposuction, for example.

In particular aspects, chondrocyte-like differentiation of human adipose cells may be facilitated by employing mechanical strain. In specific embodiments of the disclosure, upon differentiation from adipose cells, the resultant cells in vivo comprise expression of certain biochemical markers indicative of type I and II collagen and proteoglycans.

In particular aspects, chondrocyte-like differentiation of human adipose cells may occur in vivo, in which the micro-environment of the intervertebral disc is conducive for chondrocytic differentiation. Hydrostatic loading, hypoxia, cell to cell interaction with resident chondrocytic cells in the disc and other biochemical environments in the intervertebral disc may facilitate differentiation from adipose cells to chondrocytic cells, in particular embodiments. In specific embodiments of the disclosure, the cells in the intervertebral disc following cell transplantation will be a combination of adipose and chondrocytic cells that produce both adipose and chondrocytic tissues with biochemical markers of both type I and type II collagen and/or a number of proteoglycans found in cartilaginous and fibrous tissues.

In some embodiments, the adipose cells may be seeded in a matrix prior to and/or during chondrocyte differentiation and cartilage production. In embodiments wherein a matrix is employed (that may be referred to as a scaffold), the matrix may be comprised of a material that allows cells to attach to the surface of the material and form a three dimensional tissue. This material may be non-toxic, biocompatible, biodegradable, resorbable, or a combination thereof. In some embodiments, organic polymers such as polyglycolic acid (PGA), polylactic-co-glycolic acid (PLGA), poly-ε-caprolactone (PCL), polyamino acids, polyanhydrides, polyorthoesters; natural hydrogels such as collagen, hyaluronic acid, alginate, agarose, chitosan; synthetic hydrogels such as poly(ethylene oxide) (PEO), poly(vinyl alcohol) (PVA), poly(acrylic acid) (PAA), poly(propylene fumarate-co-ethylene glycol) [P(PF-co-EG) and copolymers thereof may be utilized. Alginate beads may be employed as the scaffold, in certain cases. In some embodiments, ceramic materials such as hydroxyapatite and/or tricalcium phosphate (TCP) may be used as the scaffolds in certain cases that require temporary or permanent structural support, for example. Collagen materials may be employed as the scaffold, in certain cases.

The cells may be put into a matrix made of one or more biopolymers, such as to mimic a natural matrix. The scaffold may be seeded in vitro or ex vivo, and in certain aspects growth factors are provided to the cells, the matrix, or both. The scaffold may be put into a chamber that may be a system for perfusion of medium and allows application of mechanical force to the scaffold and/or particular low oxygen conditions. Following delivery of the force, cells are assisted in differentiation, especially for generation of cartilage. In some embodiments, the matrix is employed with the cells in the mold (analogous to rebar for cement) and/or the matrix could be utilized with the adipose cells cells prior to the mold insertion.

In some aspects of the disclosure, the chondrocytes are generated and cartilage is produced in a chamber having particular conditions. The chamber may be capable of regulating one or more of the following parameters: temperature, medium pH, exchanges of gases, mechanical stimuli, $pO_2$, $PCO_2$, humidity, and nutrient diffusion, for example. A perfusion system may be present in the chamber, in specific embodiments, to provide constant supply of nutrients and to remove efficiently the waste products. One or more combinations of mechanical stresses may be provided, such as on an intermittent basis, including cell and tissue deformation, compressive and shear forces, fluid flow, and changes in hydrostatic pressure, for example. These conditions may be produced in the chamber, in certain aspects.

Adipose cells can be obtained from donor source (allogenic) or autologous skin biopsy. Isolating cells from the body and expanding them in culture may be employed, and in certain cases the cells are not manipulated or are minimally manipulated (for example, exposed to serum, antibiotics, etc). These cells can be put into a device (for example, a syringe having resuspended cells in media from a monolayer culture) and injected into the individual. Serum that is used to feed the cells for multiplication may be washed out with media such as DMEM to avoid any extraneous serum to be injected into the individual. In embodiments of this system, there is no matrix employed, including no alginate. In embodiments of the disclosure, one injects the cells only (or a minimal amount of fluid to suspend the cells for injection) and does not inject media, for example. The fluid suspension that contains the cells may comprise buffer, amino acids, salts, glucose and/or vitamins that are components of DMEM. Exemplary matrix molecules for cell manipulation that are not employed in method steps of the disclosure include polymers (including PGA, PLGA, and PCL, for example); natural hydrogels such as collagen, hyaluronic acid, alginate, agarose, chitosan, for example; and synthetic hydrogels such as PEO, PVA, PAA, etc.).

In some methods of the disclosure, following obtaining of the adipose cells one may expand the number of cells, although in alternative embodiments adipose cells are provided in vivo to an individual in need thereof in the absence of any prior expansion. The skilled artisan recognizes that cells in culture require nutrition and one can feed the cells with media, such as FBS (fetal bovine serum). Contamination or infection may be prevented (for example, by adding antibiotics), in some cases. Prior to injection of the cells to the individual, the cells are washed with DMEM media to remove FBS and antibiotics, for example, and the cells in suspension will be used for injection. The fluid suspension may contain a small amount of media including buffer, amino acids, salts, glucose and/or vitamins, for example. In vitro growth of the adipose cells cells may comprise at least one or more days for growth prior to use in vivo. In certain cases, the cells may be checked or monitored to ensure that at least some of the cells are dividing. Cells that are not dividing may be removed.

III. Mechanical Re-Differentiation of Adipose Cells and Exemplary Uses Thereof

Mechanical stress/strain are important factors for chondrogenesis. The present method uses one or more mechanical strains. Embodiments such as intermittent hydrostatic pressure (IHP), low oxygen tension, shear fluid stress, pressure load, or a combination thereof, as an inducer of chondrogenic differentiation of adipose cells. In some embodiments of the present disclosure, cells are cultured in a three dimensional matrix, for example.

Mechanical stress on adipose cells can be performed in vitro, in vivo, ex vivo, in vitro followed by in vivo, or a combination thereof. In one embodiment, the differentiation is initiated in vitro and are then implanted in vivo and continue to grow and differentiate; in some cases, the chondrocyte-like cells are seeded in the matrix (and the matrix may comprise an inert structure). The inert structure of the matrix is intended to provide a physiologic loading regimen to induce in vivo differentiation of the cells, in specific aspects of the disclosure.

In specific aspects of the disclosure, cells are induced to undergo differentiation into chrondrocytes or chondrocyte-like cells. Such differentiation may occur prior to in vivo delivery, such as on a scaffold, and/or subsequent to delivery in vivo. In specific embodiments, the cell is subjected to conditions to facilitate differentiation into chondrocytes. In a further specific embodiment, a condition comprises mechanical stress. In specific embodiments of the disclosure, mechanical stress stimulates chondrogenic differentiation of adipose cells. Such mechanical stress may be of any kind, although in specific embodiments it comprises hydrostatic pressure and/or fluid shear stress. In additional specific embodiments, the stress is constant or intermittent.

In the present disclosure, mechanical stress, such as cyclic hydrostatic pressure and shear fluid stress, induce chondrogenic differentiation of adipose cells seeded in a three dimensional matrix. The co-culture conditions to stimulate the chondrogenic differentiation may employ factors such as high cell density culture, culture with BMP-2 and ascorbic acid, and/or culture in low oxygen tension.

Methods may comprise the step of delivering adipose cells to a joint of an individual, wherein prior to delivering the adipose cells are not subjected to growth factors, matrix molecules, mechanical strain, or a combination thereof, although in alternative embodiments. The adipose cells may or may not be exposed to hypoxic conditions prior to delivery in vivo.

Embodiments of the method use in vivo mechanical strains and, in particular embodiments, uses inherent pressure from the spine to provide mechanical strain. In some embodiments, the method occurs in the absence of other types of pressure, including absence of intermittent hydrostatic pressure, shear fluid stress, and so forth. In some embodiments, the method occurs in the absence of pressure other than inherent spinal pressure, low oxygen tension, growth factors, culturing in a matrix, and so forth. In some embodiments, pressure load from the spine is employed to induce differentiation of adipose cells to other cells.

In specific aspects of the disclosure, cells are induced to undergo differentiation into chrondrocytes or chondrocyte-like cells. Such differentiation occurs subsequent to delivery in vivo, in certain embodiments. Although the cells may undergo differentiation in vivo in any joint, in specific embodiments the joint is an intervertebral disc. In aspects of the disclosure, one can improve the matrix biomechanics and biology of the disc by increasing the disc size, collagen content, and/or level of certain biological molecules. Cells in the discs, as long as they do not leak out of the space and do not die, produce matrix molecules such as collagen, proteoglycan, etc., in embodiments of the disclosure. In certain aspects, the biological molecules provide beneficial biomechanical properties, such as resisting compression/tension loadings. Cells subjected to loading with normal standing/walking/bending of the spine will differentiate into cartilaginous cells or cartilaginous-like cells in vivo. Both adipose cells and chondrocytic cells in the disc may produce fibrous and/or cartilage matrix or tissue that can improve the intervertebral disc height and volume and enhance biomechanical properties.

In certain embodiments, disc height is improved and/or certain biochemical markers are exhibited in the implanted cells. The disc height can be measured using plain radiographs, comparing before and after therapy, for example. In at least specific cases, one can also employ magnetic resonance imaging (MRI), biochemical marker assay, and/or histology. Restoring disc height improves the space for the spinal nerves that are crossing the spine, and it has an indirect benefit in this way in addition to improving the disc biomechanics and biology of the area. Histological changes following transplantation of the adipose cells can show a combination of adipose and cartilaginous cells and matrix with increased disc height because of more abundant tissue, in particular embodiments.

In some embodiments, adipose cells or re-differentiated adipose cells are injected between the vertebrae or intervertebral discs, and the cells in the nucleus pulposus may migrate to the fissures in the annulus associated disc degeneration. These cells will enhance matrix formation in both nucleus pulposus and annulus fibrosus to aid in repair and tissue regeneration. The cells in the nucleus pulposus will differentiate more toward chondrocytic and the cells in the annulus fibrosus will be more adipocytic due to mechanical and biochemical environments of the nucleus pulposus and annulus fibrosus, in certain embodiments.

In some embodiments, differentiation of the adipose cells does not begin until implantation in vivo and not all of the transplanted cells can differentiate into chondrocytic cells because of varying biomechanical and biochemical environments.

In embodiments of the disclosure, one obtains adipose cells, for example from the individual being treated, obtains them from another individual (including a cadaver or living donor, for example), or obtains them commercially. One can take a fat biopsy and in some embodiments may manipulate the fat biopsy. For example, one can digest the fat tissue overnight to get adipose cells, culture the cells to expand, and provide them to the individual, including by injecting them into the individual, for example. Prior to delivery to the individual, the cells may be passaged one or more times depending on the number of cells needed, including 1, 2, 3, 4, 5, 6, 7, 8, 9, 10, or more times, for example. Passaging may occur over the course of one or more days, including 2, 3, 4, 5, 6, 7, 8, 9, or 10 days, or 1, 2, 3, 4, or more weeks, for example. In some embodiments, the cells are passaged for 5-7 days, for example.

In embodiments of the disclosure, intervertebral disc disease is prevented by providing adipose cells in vivo to an individual in need thereof, including an individual susceptible to the disease, for example an aging individual. In some embodiments, the individual is an adult. An individual at risk for the disease includes an athlete (professional or recreational), smokers, obese individuals, and/or those whose occupations or lifestyle require physical labor, including excessive lifting, for example.

IV. Support Embodiments

In particular embodiments of the disclosure, adipose cells or re-differentiated adipose cells, are delivered to an individual with one or more supports. The cells may be delivered with a support when the cells are in the form of tissue, and in some cases the tissue is of a desired shape.

In some cases, cartilage generated by the methods of the disclosure is provided in vivo to an individual in conjunction with one or more supports for the cartilage. The support may be biodegradable or non-biodegradable and/or resorbable or non-resorbable, depending upon need. In cases where the support is resorbable, the support material may be of any kind in the art, including biopolymer. Lactide-based polymers including synthetic polyesters such as polylactide and copolymers with glycolide and ε-caprolactone are examples of resorbable polymers. In cases where the support is non-resorbable, the support material may be of any kind in the art, including metal or polymer. Non-resorbable polymers include polyacetal resins and/or polyetheretherketone. Slowly resorbable materials, such as ceramics and collagen, may be used for support.

Cartilage may be generated in vivo through an implantable reservoir or container used for the purpose of chondrogenic cell formation, and the reservoir can be removed after cartilage has formed, or the container may be made of absorbable materials that will be reabsorbed by the body during and after cartilage formation.

The support may be of any shape, including a shape that conforms to the shape of the cartilage, in some cases. The shape of the support may be a substantially identical shape of the support. In some cases, the support does not conform to the cartilage shape but is still supportive in function. Some support shapes include linear, round, tubular, rectangular, spherical, screw-like, conical, threaded, cup, box, and so forth.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Adipose Cell Injection and In Vivo Differentiation

In embodiments of the disclosure, adipose cells are delivered to mammalian vertebrae to improve intervertebral disc degeneration, for example. In some embodiments, adipose cells are delivered to mammalian vertebrae to induce chondrocyte differentiation or to continue chondrocyte differentiation.

A rabbit model is employed that involves puncturing the annulus, which reduces the disc height (due to matrix loss and degeneration, for example) to about 70% normal height about 4 weeks after the injury. The cell transplantation in this model is performed at 4 weeks following the annulus puncture, and the disc height gradually increases, for example for the next 3-4 weeks. The cells that were injected are contained in the disc and are alive to make more matrix (adipose and cartilaginous tissue) to increase the disc height. The more matrix and increased disc height results in better biomechanical function and less pain for the individual. In certain aspects, biochemical analysis shows that type I and type II collagen is expressed, which shows that there is cartilaginous component, indicating that at least in some cases there is cartilaginous tissue (if it were all fibrous (scar tissue), type I collagen without type II collagen would be mainly expressed, but cartilaginous tissue expresses type II collagen).

Upon manipulation of the above-referenced rabbit model, the disc height increases following transplantation of the adipose cells.

Example 2

Ex Vivo Production of Cartilage from Adipose Cells

An individual in need of cartilage or suspected of being in need of cartilage is subjected to method(s) of the disclosure. An individual in need of cartilage, such as having missing or defective cartilage, for example, is subjected to method(s) of the disclosure. In specific embodiments, an individual is diagnosed as being in need of cartilage. In some embodiments, the individual is not in need of vertebral disc repair.

Adipose cells are obtained from another individual or commercially. The adipose cells may be cultured after being obtained. The adipose cells may be subjected to conditions that facilitate chondrocyte differentiation, such as low oxygen, mechanical stress, or a combination thereof.

In some cases, the defective cartilage or a representative of the defective cartilage (such as a mirror image of the defective cartilage, for example in a knee, shoulder, or ear) is imaged with appropriate methods, such as an MRI or CT scan, for example. The image is then employed to generate a mold of the desired shape of the defective cartilage. The adipose cells are provided to the mold, and as the mold/adipose cells are subjected to appropriate conditions, the adipose cells differentiate into chondrocytes in the mold to produce cartilage tissue. In specific embodiments, however, the adipose cells alone are subjected to appropriate conditions to produce chondrocytes prior to seeding in the mold, and in some cases the adipose cells are subjected to appropriate conditions to produce chondrocytes prior to and following seeding in the mold. The mold itself may be able to generate the conditions necessary or the mold may be inserted into another container that generates those conditions.

The resultant cartilage is provided to an individual in need thereof, including the same individual from which the adipose cells were harvested and/or to another individual in need of cartilage repair. In specific embodiments, the cartilage tissue is combined prior to or upon delivery with one or more supports to facilitate secure placement of the cartilage in its desired location, although in some cases a support is not needed. The support may be resorbable or may not be resorbable, depending on the desired location, thickness of the cartilage, and so forth.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of inducing de-differentiation of adipose cells to chondrocyte-like cells, comprising the steps of:
    obtaining differentiated adipose cells from an individual; and
    inducing de-differentiation of the differentiated adipose cells to chondrocyte-like cells by subjecting the adipose cells to mechanical strain.

2. The method of claim 1, wherein the subjecting step occurs in vitro or ex vivo.

3. The method of claim 2, wherein when the subjecting step occurs in vitro, the cells are combined with a scaffold to produce a cells/scaffold composition.

4. The method of claim 3, wherein the cells/scaffold composition comprises growth factors, matrix molecules, drugs, or a combination thereof.

5. The method of claim 3, wherein the cells/scaffold composition is delivered to an individual.

6. The method of claim 5, wherein the cells/scaffold composition is delivered to the joint of an individual.

7. The method of claim 6, wherein the joint is an intervertebral disc.

8. The method of claim 7, wherein the individual has intervertebral disc disease.

9. The method of claim 2, wherein when the subjecting step occurs ex vivo, the cells are provided conditions suitable to generate cartilage.

10. The method of claim 9, wherein the conditions comprise low oxygen, mechanical stress, or a combination thereof.

11. The method of claim 9, wherein the cartilage is configured in the form of a desired shape.

12. The method of claim 11, wherein the desired shape is at least part of an ear or of a nose.

13. The method of claim 11, further comprising the step of generating a mold of the desired shape.

14. The method of claim 11, further comprising the step of providing the cartilage to an individual that is in need of cartilage repair.

15. The method of claim 14, wherein the cartilage is provided to the individual with one or more supports.

16. The method of claim 15, wherein the support is resorbable.

17. The method of claim 15, wherein the support is comprised of a material that would be resorbed by the body of the individual during and/or after its function of cartilage formation is completed.

18. The method of claim 15, wherein the support is non-resorbable.

19. The method of claim 18, wherein the support is comprised of metal or one or more other materials that may remain in the body and promotes maintenance of shape and function of the cartilage.

20. The method of claim 14, wherein the cartilage tissue is delivered to a nose, ear, knee, shoulder, elbow or other area of the body where connective tissue is required for the individual.

21. The method of claim 14, wherein the cartilage tissue is not delivered to a joint.

22. The method of claim 14, wherein the cartilage tissue is not delivered to a vertebral disc.

23. The method of claim 11, wherein said desired shape replaces or repairs cartilage in one or more regions of the body of an individual, wherein said region requires connective tissue.

24. The method of claim 11, further comprising the step of imaging a part of the body of an individual that is in need of cartilage repair or that is at risk of being in need of cartilage repair.

25. The method of claim 11, further comprising the step of imaging a part of the body of an individual that is in need of cartilage repair and generating therefrom a mold of a desired shape of cartilage.

26. The method of claim 11, further comprising the step of imaging a part of the body of an individual wherein that part is not in need of repair and generating from that image a mold for growth of cartilage to replace or repair an area in need of repair.

27. The method of claim 1, wherein the subjecting step occurs in vivo in an individual.

28. The method of claim 27, wherein when the subjecting step occurs in vivo, the adipose cells are not subjected to growth factors, matrix molecules, mechanical strain, or a combination thereof prior to the in vivo subjecting step.

29. The method of claim 27, wherein the adipose cells are delivered to a joint of the individual.

30. The method of claim 29, wherein following delivery to the joint, there is a mixture of adipose cells and chondrocyte-like cells in the joint.

31. The method of claim 29, wherein the adipose cells are delivered between vertebral discs.

32. The method of claim 29, wherein the adipose cells are delivered between or in nucleus pulposus and fissures in the inner annulus fibrosus.

33. The method of claim 29, wherein following delivery of the adipose cells to the joint of the individual, a plurality of adipose cells die.

34. The method of claim 33, wherein death of the adipose cells results in a cellular response from endogenous joint cells of the individual.

35. The method of claim 34, wherein the cellular response comprises stimulation of growth of the endogenous joint cells of the individual.

36. The method of claim 29, wherein following delivery of the adipose cells to the joint of the individual, there is development of scar tissue in the joint.

37. The method of claim 27, wherein the individual has intervertebral disc disease.

38. The method of claim 27, wherein the cells are delivered to an intervertebral disc.

39. The method of claim 27, wherein the cells are autologous or allogeneic to the individual.

40. The method of claim 1, wherein the mechanical strain comprises low oxygen tension, intermittent hydrostatic pressure, fluid shear stress, or a combination thereof.

41. The method of claim 1, wherein the adipose cells are white adipose cells, brown adipose cells, or a mixture thereof.

42. The method of claim 1, wherein the obtained adipose cells are expanded.

43. The method of claim 42, wherein the obtained adipose cells are expanded for at least one day.

44. The method of claim 1, wherein the obtained adipose cells are passaged.

45. The method of claim 44, wherein the passaging occurs more than once.

46. A method of inducing de-differentiation of adipose cells to chondrocyte-like cells, comprising the steps of
   obtaining differentiated adipose cells from an individual; and
   inducing de-differentiation of the differentiated adipose cells to chondrocyte-like cells by subjecting the adipose cells to mechanical strain, wherein the mechanical strain comprises low oxygen tension, intermittent hydrostatic pressure, fluid shear stress, or a combination thereof.

47. The method of claim 46, wherein the cells are combined with a scaffold to produce a cells/scaffold composition.

48. The method of claim 47, wherein the cells/scaffold composition is delivered to the joint of an individual.

49. The method of claim 48, wherein the joint is an intervertebral disc.

50. The method of claim 46, wherein the cells are autologous or allogeneic to the individual.

* * * * *